United States Patent [19]

Hsu

[11] Patent Number: 4,769,007
[45] Date of Patent: Sep. 6, 1988

[54] AUTOMATIC SHUTTING-OFF SEALING AND ALARMING DEVICE FOR DRIPPING INJECTION USE

[76] Inventor: Shun-Fa Hsu, No. 1, Ping Ho 9th Road, Hsiao Kang Dist., Kaohsiung City, Taiwan

[21] Appl. No.: 29,583
[22] Filed: Mar. 25, 1987
[51] Int. Cl.⁴ ............................................. A61M 1/00
[52] U.S. Cl. .................................. 604/127; 604/251; 604/256
[58] Field of Search ........................ 604/127, 251, 256

[56] References Cited

U.S. PATENT DOCUMENTS

| | | | |
|---|---|---|---|
| 3,216,419 | 11/1965 | Scislowicz | 604/127 |
| 3,227,173 | 1/1966 | Berstein | 604/127 |
| 4,203,463 | 5/1980 | Ponlot et al. | 604/127 |
| 4,244,364 | 1/1981 | Grushkin | 604/127 |
| 4,449,976 | 5/1984 | Kamen | 604/127 |

FOREIGN PATENT DOCUMENTS 2409339  9/1975  Fed. Rep. of Germany ...... 604/127

Primary Examiner—C. Fred Rosenbaum
Assistant Examiner—Gene B. Kartchner
Attorney, Agent, or Firm—Browdy & Neimark

[57] ABSTRACT

Present disclosure relates to an automatic shutting-off and alarming device for dripping injection use, which comprises of a closed container, a buoyant cylinder, a ring magnet, a magnetically actuated contactor, and an alarming system. The ring magnet is furnished on the bottom end of the buoyant cylinder and the buoyant cylinder is placed into the closed container, the magnetically actuated contactor is pivotally clamped to the bottom edge of the closed container. When injection fluid comes into the closed container, buoyant force keeps the buoyant cylinder afloat, and when the injection fluid is almost used up, the fluid level of the closed container is lowered down, and the magnetic forces between the ring magnet on the bottom end of the buoyant cylinder and the magnet on the magnetically-actuated contactor attracts each other for shutting-off the injection fluid to stop the injection as well as to activate an alarming system for alerting the nurse or medical care personnel in the nursing shift center to take proper action. The device not only can secure the injection safety, it also saves manpower for patient's care, saves time for subsequent injections, and promotes to hospital management.

4 Claims, 5 Drawing Sheets

AUTOMATIC SHUTTING-OFF SEALING AND ALARMING DEVICE FOR DRIPPING INJECTION USE

SUMMARY OF THE INVENTION

An automatic shutting-off and alarming device for dripping injection use, in particular, by combining both buoyant force and magnetic attracting force to provide injection fluid with automatic shutting-off when the injection fluid is almost used up, and to alert the nurse or medical care personnel in the nursing shift center to take proper action to the patient for ensuring the injection safety, saving manpower for patient's care, saving time for subsequent injections, and promoting the hospital management.

Dripping injection fluids are general-purpose medicines they are utilized via blood vessel injection for patient's need. In a traditional blood vessel dripping injection equipment, the dripping injection fluid comes from a dripping bottle, through a guiding tube, a dripping nozzle and flow rate control valve, and an injection needle, then goes into the blood vessel of a patient, this traditional blood vessel dripping injection fluid and equipment has been utilized for a long time by doctors for patient treatment or patient body strength and spirits maintenance, though it works well, but still has shortcomings as follows:

1. Since the dripping injection fluid is pumped into the blood vessel by atmospheric pressure and gravitational force, therefore, in order to maintain patient's safety and to prevent accident, a patient under dripping injection treatment is closely watched by other dedicated person, further more, a bottle of dripping injection usually requires several hours to finish the injection, also one bottle after another bottle subsequent injections are commonly required, therefore, dripping injection becomes a tiresome and time-consuming work.

2. As time goes by, in a busy business and industrial age, spending a lot of time to accompany a patient becomes an expensive burden.

3. Because traditional dripping injection are taken care by people who accompanies the patient, therefore, accident may happen due to sleep or neglect.

4. When dripping injection fluid is almost used up and the fluid level lowers down under the dripping valve, if subsequent injection is continuous, the trapped air shall exist between the old injection fluid and the new injection fluid, under this condition, in order to remove the trapped air, and secure the patient's safety, the injection needle should be removed from the patient's blood vessel, until the old injection fluid and trapped air are all drained out and new injection fluid comes out from the injection needle tip, then the injection needle is pierced into the patient's blood vessel again for subsequent injection, in this manner, the patient cannot but suffer piercing pain once again.

5. Though, there are electronic surveillance equipments for dripping injection are available nowaday, but these equipments are short of automatic stop devices. Not only they are complex in structure, power consuming, limited by power source requirement, expensive, high out of order rate, and difficulty in maintenance, but also they has no any contactors for using to alert the nurse or medical care personnel in the nursing shift center.

Based on these findings, the inventor provides a new automatic shutting-off and alarming device for dripping injection use, this new device not only removes all above-mentioned shortcomings, it is also a safe, practical, reliable, time saving, and economical device to be widely adapted for medical application.

The main purpose of present invention is to provide an automatic shutting-off and alarming device for dripping injection use, in particular, which comprises of a closed container, a buoyant cylinder, a ring magnet, a pivotally clamped magnetically-actuated contactor, an alarming system. This device can alert the medical personnel to take immediate action for a patient when the dripping injection fluid is almost used up, and it is also advantageous for the promotion of management of a hospital, and these advantages constitute the specific feature of the present invention.

The other purpose of the present invention is to provide an automatic shutting-off and alarming device for dripping injection use, of which, the buoyant cylinder lowers down to shut-off the injection fluid when the injection fluid is almost used up for securing the injection safety, this advantage also constitues another specific feature of present invention.

Another object of the present invention is to provide an automatic shutting-off and alarming device for dripping injection use, of which, when the buoyant cylinder is lowered down to shut off the injection fluid, at the same time, the magnetic force between the ring magnet on bottom side of the buoyant cylinder and the pivotally clamped magnets of the magnetically-actuated contactor activates two alarming signals, one for patient's bedroom and other for nursing shift center, to alert the medical personnel to take proper action for the patient for saving the nursing manpower and time, this advantage also constitutes the specific feature of present invention.

Still another purpose of the present invention, is to provide an automatic shutting-off and alarming device for dripping injection use, of which, the center portion on bottom side of the buoyant cylinder is formed into a conical shape, this conical shaped structure incoorparates with the outlet port of the closed container constituting a shutting-off valve, and this valve is actuated by both gravitational and magnetic force to shut off the injection fluid when it is almost used up, it can also prevent the blood from reversed flow into the dripping injection tube of a patient, when the blood pressure in increased abruptly at this time. This advantage also constitutes one of the specific feature of the present invention.

One further object of the present invention is to provide an automatic shutting-off and alarming device for dripping injection use, of which, when the injection fluid is shutted off during the injection fluid is almost used up, both the closed container and the tube lines of the dripping injection equipment still maintains enough injection fluid, and subsequent injection fluid bottle can be connected to it directly, consider any trapped air to be injected into patient's vessel is not necessary. This advantage also constitutes one of the specific feature of present invention.

The structure, function, and characteristics of the present invention are described in detail with the attached drawings as follows:

DETAILED DESCRIPTION

Figure 1:
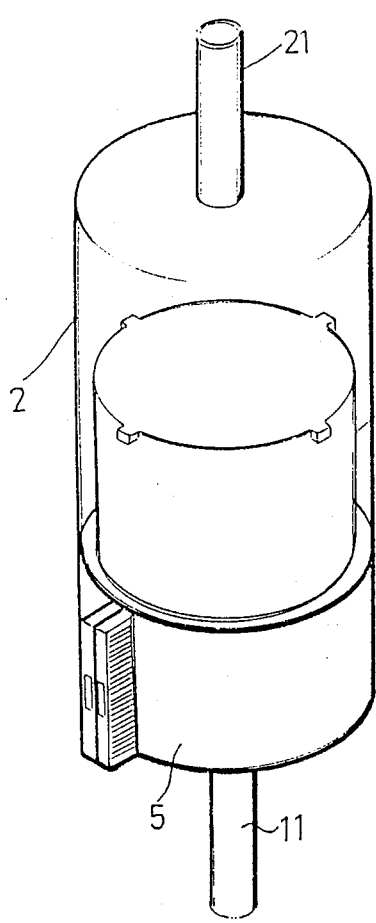
FIG. 1 shows the perspective view of the automatic shutting-off and alarming device for dripping injection use of the present invention.
Figure 2:
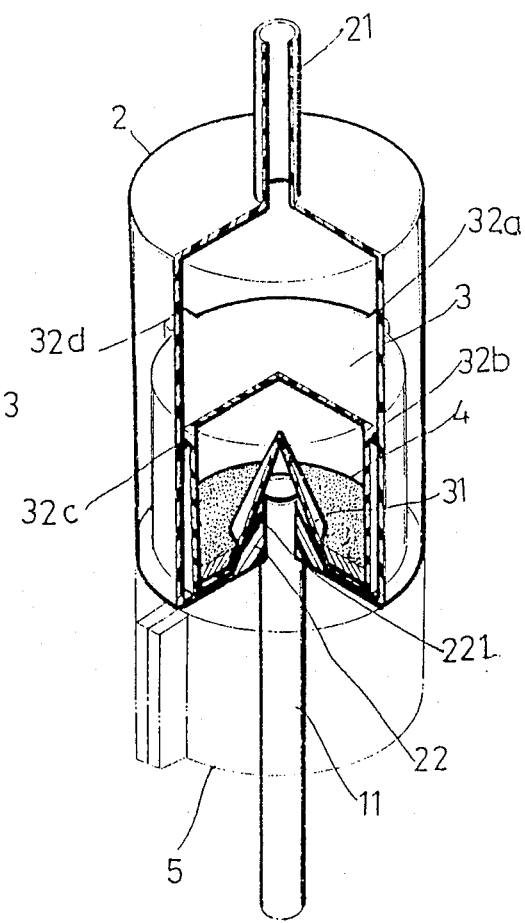
FIG. 2 shows the sectional perspective view of the closed container and the buoyant cylinder for the automatic shutting-off and alarming device for dripping injection use of the present invention.
Figure 3:
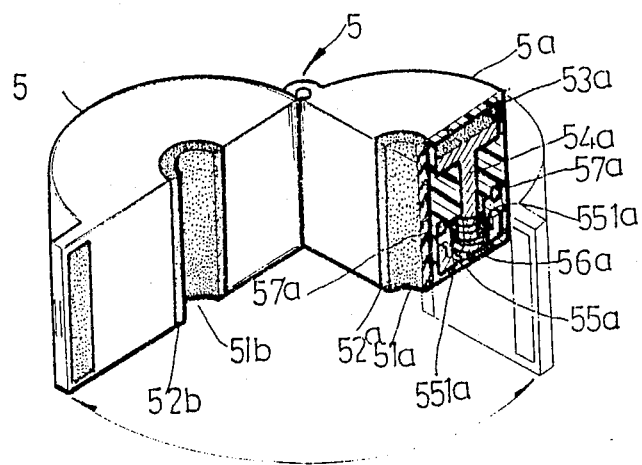
FIG. 3 shows the sectional perspective view of the a magnetically-actuated contactor for the automatic shutting-off and alarming device for dripping injection use of the present invention.

Refer to FIG. 1 to 3, the automatic shutting-off and alarming device for dripping injection use of the present invention comprises of a closed container 2, a buoyant cylinder 3, a ring magnet, a magnetically-actuated contactor 5, and an alarming device, in which, the closed container 2 is made of transparent soft PE plastic material, and this closed container 2 has an inlet tube 21 on its top end, for connecting a needle which is inserted into the injection fluid bottle and a cone-shaped outlet port 22 and a socket 221 on its bottom end for plugging in an injection fluid output tube. A buoyant cylinder 3 with multiple guiding ears 32a, 32b, 32c and 32d is placed into this closed container 2, the buoyant cylinder 3 has a ring magnet 4 which is fixed onto its bottom end, on the same bottom end it is integratedly moulded with the buoyant cylinder body 3 a conical portion 31, and this conical portion can fit water tightly with the conical port 22 of the closed container 2.

The magnetically actuated contactor 5 comprises of two symmetrical contactor bodies 5a, 5b, and an integrated magnetically actuated contactor 5 is assembled by clamping this two contactor bodies together, the inner walls around the two central half-openings 51a and 51b are furnished with rubber layers 52a and 52b, they are utilized to tighten the injection fluid out-flowing tube when the magnetically-actuated contactor 5 bodies is clamped together. Two semi-ring magnets 53a and 53b, are furnished respectively on the upper ends of each of the contactor bodies 5a and 5b, the bottom ends of these semi-ring magnets are attached respectively to their connecting rods 54a and 54b, the bottom ends of these connecting rods 54a and 54b are attached to their respective movable arms 55a and 55b, two coiled springs 56a and 56b are furnished respectively under each movable arms 55a and 55b, also contact points 551a, 551b, are furnished on top sides of movable arms and corresponding contact points 57a, 57b are furnished on bottom side of the contactor bodies as they are facing he contacting points 551a and 551b on contact arms 55a and 55b, these structural components forms an integrated magnetically-actuated contactor further more, the polarities on top sides of each of the semi-ring magnets 53a, 53b of the magnetically-actuated contactor are just the reversal to the polarities on bottom side of the ring magnet on bottom end of the buoyant cylinder, therefore, attractive force is activated between them when injection fluid is almost used up which in turn activates the contact points 57a and 57b to produce alarming signals.

Figure 4:
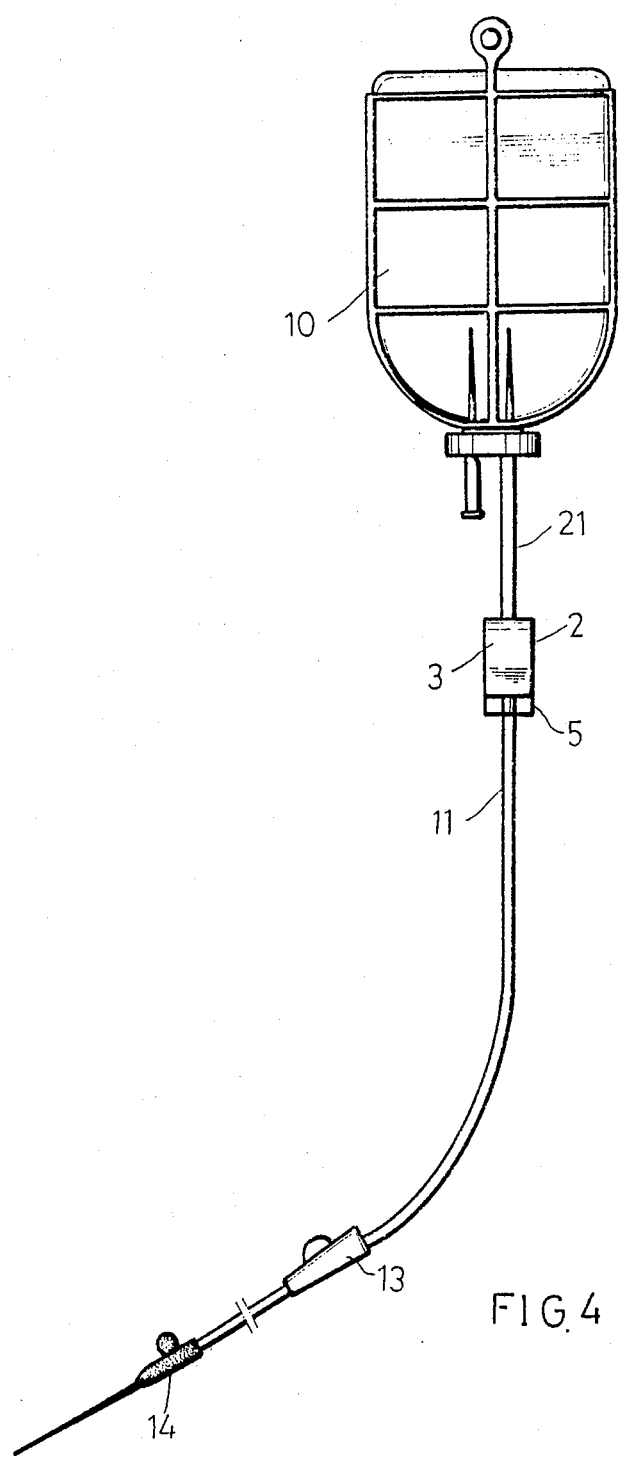
FIG. 4 shows the implementation diagram of the automatic shutting-off and alarming device for dripping injection use the present invention.
Figure 5:
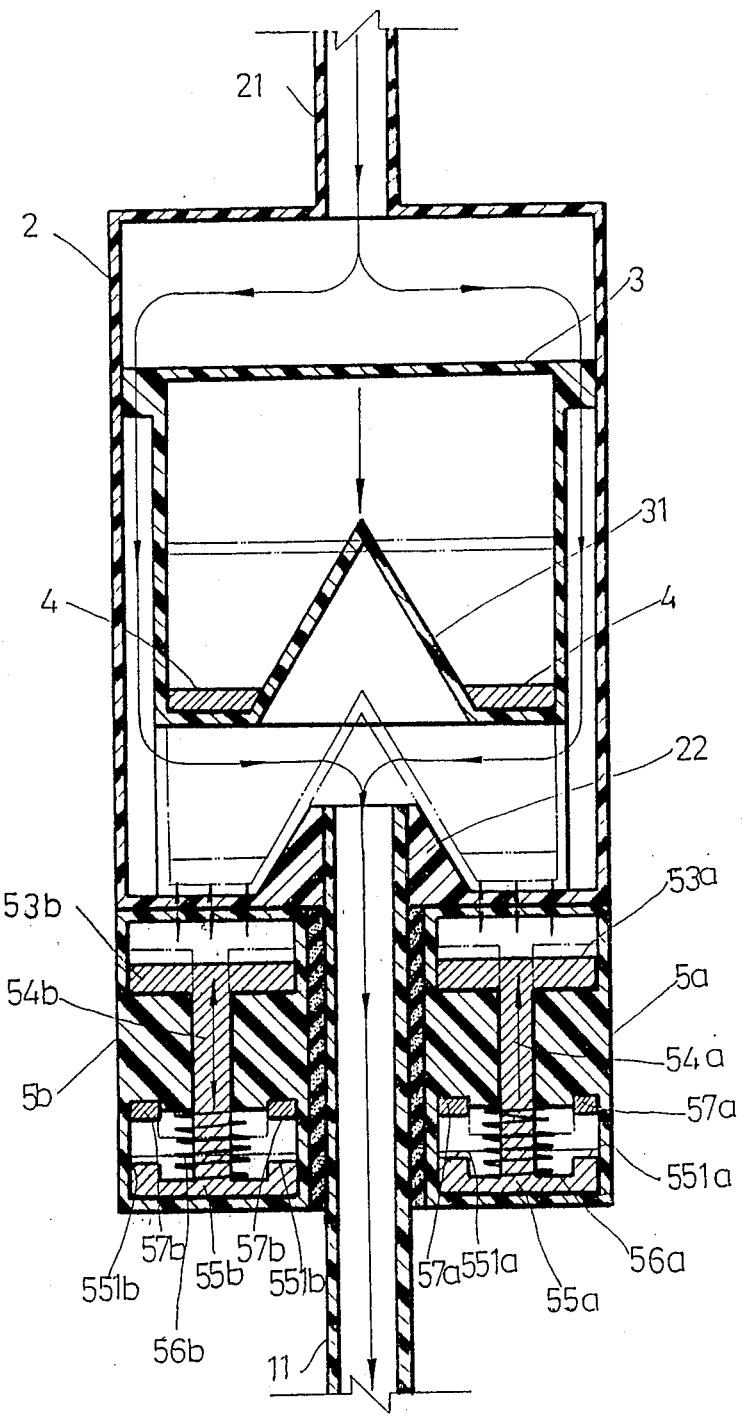
FIG. 5 shows the sectional view of the automatic shutting-off and alarming device of the present invention with functions illustrated.
Figure 6:
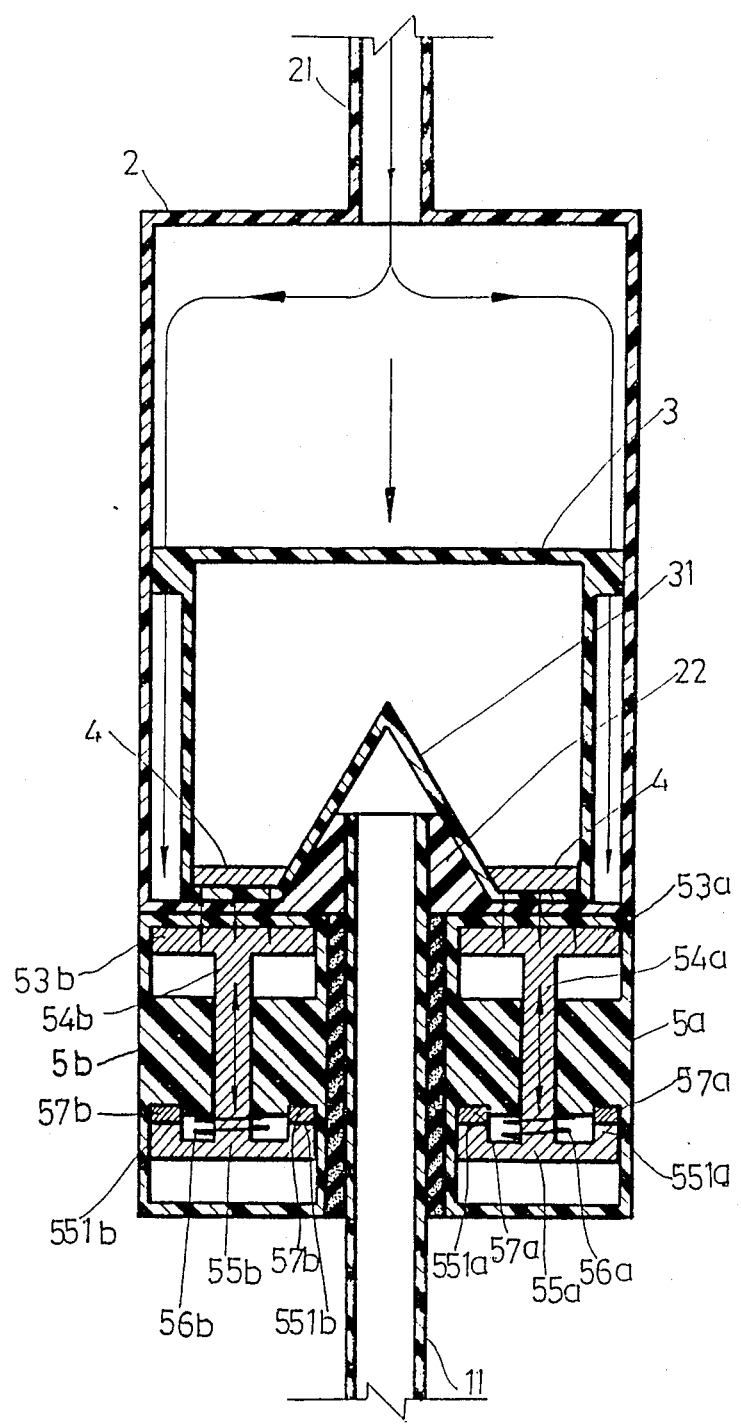
FIG. 6 shows the sectional view of the automatic shutting-off and alarming device for dripping injection use of the present invention with shutted-off position as illustrated.
Figure 7:
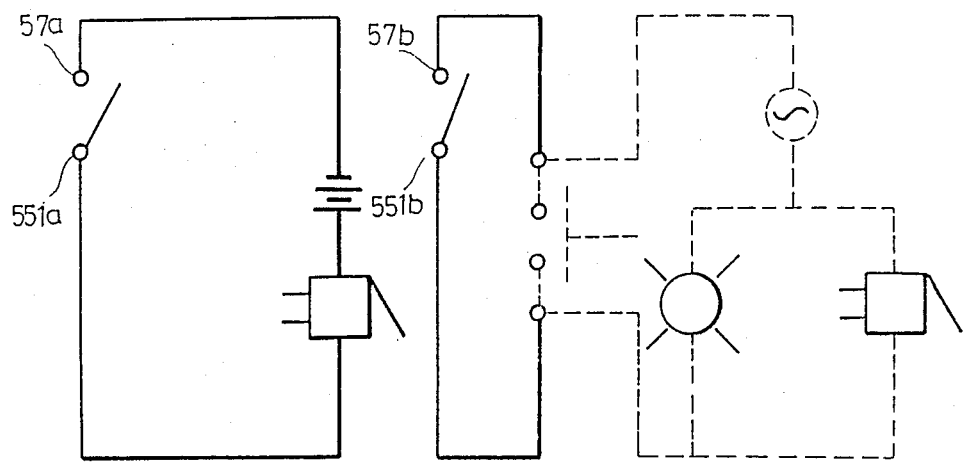
FIG. 7 shows the circuit diagram for the embodiment example of the alarming system of the automatic shutting-off and alarming device for injection use of the present invention; Contactor 57b, 551b shall be connected to the hospital existing equipments, which are shown in dotted lines, such as emergency push button that connected to the nursing shift center or any medical instruments.

Refer to FIG. 4, the automatic shutting-off and alarming device for dripping injection use of the present invention utilizes the guiding tube 21 on top of the closed container 2 to connect the injection fluid bottle 10 via a needle, when injection fluid comes into the closed container 2, buoyant force causes the buoyant clyinder 3 to float upwardly, in addition, an injection fluid guiding tube 11 is inserted into thefluid outlet socket 221 to lead the injection fluid into the flow rate control switch 13, needle 14, then goes into the blood vessel of a patient, since magnetically actuated contactor 5 is clamped to the injection fluid guiding tube 11 at the bottom end of the closed container 2, at this time, the gravitational force plus the spring force of coiled spring 56a, 56b acting on semi-ring magnets 53a and 53b, connecting rods 54a and 54b, and movable arms 55a and 55b cause them to fall downwardly to break off the connection of each pair of contact points (as shown in FIG. 5). When the injection fluid in almost used up, the injection fluid level in the closed container will gradually lower to a certain level, so does the buoyant cylinder 3, at this time, the distance between the ring magnet 4 and the semi-ring magnets 53a and 53b reaches it's shortest, thus maximum attracting force activated between them, which pulls instantly the conical portion 31 on bottom end of the buoyant cylinder 3 down, over the conical outlet port 22 of the closed container 2 to shut off the fluid from going into the socket 221 for stopping the dripping injection in one way, and pulls instantly the contact points 511a and 511b on movable arms 55a and 55b up to connect points 57a and 57b on bottom side of contactor bodies via semi-ring magnets 53a and 53b, connecting rods 54a and 54b, and movable arms 55a and 55b in another way to activate the alarming device (as shown in FIG. 7) for issuing two alarm signals, one for patient's bedroom and other one for nursing shift center, to alert the medical personnel to take proper action for the patient. At this time, if subsequent injection is not required, the only thing to do is the detachment of the magnetically actuated contactor 5, once the magnetically-actuated contactor 5 is detached from the bottom end of the closed container, no more strong magnetic attracting force is exerted on the movable arms 55a and 55b since the movable arms 55a and 55b are connected to the semi-ring magnets 53a and 53b on top side of the magnetically-actuated contactor bodies 5a and 5b via the connecting rods 54a and 54b, therefore, the gravitational force plus the spring force of the coiled spring 56a and 56b pull the movable arms 55a and 55b down and breads the connection between contact point pairs 551a and 57a, 551b and 57b, and the alarming signals are stopped, then removes the needle from the blood vessel of the patient to complete the dripping injection process. From above description it can be seen that present invention can complete a safety dripping injection without any people staying beside a patient, also the alarming device can be connected to a ward, a nursing station, or a nursing shift center for an integrated monitoring management for multiple dripping injections to save time and manpower for patient's care.

Figure 8:
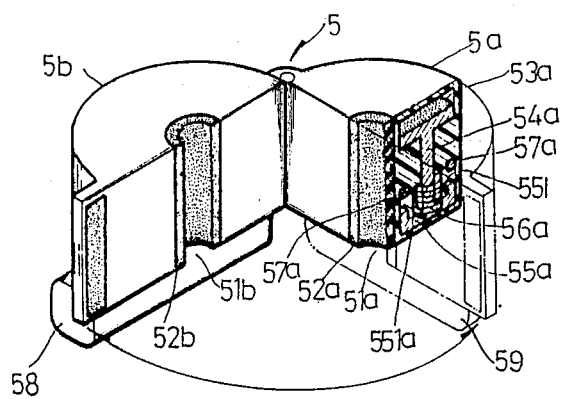
FIG. 8 shows another embodiment example of magnetically-actuated contactor for alarming device of the automatic shutting-off and alarming device for dripping injection use of the present invention.

Since strong magnetic force exists between ring magnet 4 and two semi-ring magnets 53a and 53b when the distance between them is shortened, therefore, when the injection fluid is almost used up and the injection fluid in the closed container 2 is lowered to a certain level, so does the buoyant cylinder 3, at this time, the distance between above-mentioned magnets is shortened and strong magnetic force is activated between them, this strong magnetic force not only pulls the buoyant cylinder 3 down instantly to close down the injection fluid flowing passage it also pulls the movable arms 55a and 55b up to connect the contact point pair 551a and 57a, and contact point pair 551b and 57b for the issuing of alrming signals. When the injection fluid flowing passage is closed up by this magnetic force, the injection fluid level in the closed container 2 is about the same as the floating level of the buoyant cylinder 3, at this time, if subsequent dripping injection is not required, what the medical care personnel is going to do then is to pull out the injection needle from the blood vessel of the patient, and detaches the magnetically-actuated contactor 5 from the bottom end of the closed container 2 to conclude the dripping injection, if subsequent dripping injeciton is required, what the medical care personnel is going to do then is to remove the guiding tube needle from the empty injection fluid bottle, and inserts it into a new injection fluid bottle, when injection fluid coming into the closed container reaches a certain level, then detaches the magnetically-actuated contactor 5 from the bottom end of the closed container 2 to open the injection fluid flowing passage for starting subsequent dripping injection, after buoyant cylinder 3 has risen up from the closing-down position, then attaches the magnetically-actuated contactor 5 again to the bottom end of the closed container to recover it's alarming function. In this manner, because there is no any trapped air exists between the old tripping injection fluid and new tripping injection fluid, so the injection needle needs not to be pulled out from the blood vessel for removing the trapped air and inserts it back again. Further more a battery compartment 58 and a buzzer 59 can be furnished on bottom side of the magnetically-actuated contactor 5 as shown in FIG. 8, in this way, the present invention possesses a self-powered alarming system.

The closed container of the present invention is intentionally to be utilized as a substitute for the dripping valve, and this closed container combines with the functions of the buoyant cylinder, magnetically-actuated contactor and the alarming device making the present invention, the automatic shutting-off and alarming device for dripping injection use, a safe, practical, and advanced injection system with advantages as follows:

(1) When the injection fluid is almost used up, it shuts up the injection fluid from injection and alarms the medical care personnel in the nursing shift center to take proper action for the patient.

(2) It can be shunt with the emergency pushbutton near the patient's bedroom to the nursing shift center for integrated patient's management.

(3) Subsequent injection can be carried on continuously and smoothly without any unsafe factor.

(4) Battery can be utilized to supply the alarming signal power, it consumes electric power only for the buzzer when the injection fluid is almost used up, and it does not need any electric power during dripping injection period.

(5) Simple in structure, small in volume, convenient in storage, carry and utilization.

(6) Low production cost, and practical in utilization.

I claim:

1. An automatic shutting-off and alarming device for dripping injection use, which comprises of:
a closed container, which is an empty body made of transparent plastics, the top end of this empty body being furnished with a fluid guiding tube for connection to a bottle containing dripping injection fluid, the bottom end of this empty body is furnished with an injection fluid outlet socket for plugging in an injection fluid guiding tube;
a buoyant cylinder, which is installed into the above-mentioned closed container to provide buoyant force;
a ring magnet, which is attached to the bottom end of the buoyant cylinder;
a magnetically-actuated contactor, which comprises two symmetrical contactor bodies, pivotally connected and clamped together into an intergrated contractor body, the central portion of these symmetrical contactor bodies being furnished respectively, with a semi-ring tightening bore the top side of each symmetrical contactor body being furnished with a semi-ring magnet, a movable arm, having on each top side a contact point, being attached firmly to each of the above-mentioned semi-ring magnet via a connecting rod, a coiled spring to furnish under the bottom side of each movable arm, two contact points, one on each side, just opposite to and matching to the above-mentioned contact points being furnished on the bottom surface at the intermediate section of the magnetically-actuated contactor, with the above-mentioned structural components, and the magnetically-actuated contactor attaches to the bottom end of the closed container by clamping it at the injection fluid guiding tube, below the closed container, the dripping injection being able to automatically shut off by strong magnetic attracting force between ring magnet on hottom side of buoyant cylinder and semi-ring magnets on top sides of magnetically-actuated contactor when the buoyant cylinder is lowered down to a certain level at which the injection fluid is almost used up as well as the same magnetic attracting force pulling the movable arms up to close the above-mentioned contact points and producing two alarming signals, one for patient's bedroom and other for nursing shift center, to alert the medical care personnel to take immediate action for the patient.

2. An automatic shutting-off and alarming device for dripping injection use as set forth in claim 1, in which, the polarities between the ring magnet on bottom end of the buoyant cylinder and the semi-ring magnet contactor bodies are reversal to each other.

3. An automatic shutting-off and alarming device for dripping injection use as set forth in claim 1, in which, the outlet port on inner bottom side of the closed container and the bottom side of the buoyant cylinder are formed into conical shape for firmly shutting-off the injection fluid when the dripping injection fluid is almost used up.

4. An automatic shutting-off and alarming device for dripping injection use, as claimed in claim 1, wherein the automatic shutting-off and alarm performances are carried out by way of said buoyant object combined with magnetic force at the impending termination of the injection process.

* * * * *